(12) United States Patent
Kavanagh et al.

(10) Patent No.: US 8,523,843 B2
(45) Date of Patent: Sep. 3, 2013

(54) VAPOR HYDRATED CATHETER ASSEMBLY AND METHOD OF MAKING SAME

(75) Inventors: Seamus T. Kavanagh, Libertyville, IL (US); Bettakeri S. Udayakumar, Darien, IL (US); James J. Passalaqua, Salem, WI (US); Kai Jorgensen, Copenhagen (DK); Thomas H. Gilman, Spring Grove, IL (US)

(73) Assignee: Hollister Incorporated, Libertyville, IL (US)

( * ) Notice: Subject to any disclaimer, the term of this patent is extended or adjusted under 35 U.S.C. 154(b) by 913 days.

(21) Appl. No.: 12/100,916

(22) Filed: Apr. 10, 2008

(65) Prior Publication Data

US 2009/0131917 A1   May 21, 2009

Related U.S. Application Data

(60) Provisional application No. 60/988,920, filed on Nov. 19, 2007.

(51) Int. Cl.
*A61M 27/00* (2006.01)

(52) U.S. Cl.
USPC .......................................... 604/544; 206/364

(58) Field of Classification Search
USPC .................. 604/544, 349, 327, 329; 206/364
See application file for complete search history.

(56) References Cited

U.S. PATENT DOCUMENTS

| | | | |
|---|---|---|---|
| 2,307,736 A * | 1/1943 | Clunan | 229/87.05 |
| 2,360,597 A | 10/1944 | Topolski | |
| 2,947,415 A | 8/1960 | Garth | |
| 3,012,481 A | 12/1961 | Hughes | |
| 3,035,691 A | 5/1962 | Rasmussen et al. | |
| 3,286,832 A | 11/1966 | Pilger | |

(Continued)

FOREIGN PATENT DOCUMENTS

| AU | 706432 B2 | 6/1999 |
|---|---|---|
| CH | 677094 | 4/1991 |

(Continued)

OTHER PUBLICATIONS

European Search Report issued in counterpart European Patent Application No. 08103085.0 (7 pages), Aug. 12, 2008.

(Continued)

*Primary Examiner* — Susan Su
(74) *Attorney, Agent, or Firm* — Cook Alex Ltd.

(57) ABSTRACT

A catheter assembly and method is disclosed which comprises a catheter having a coating on at least a part of its length intended to produce a low-friction surface on the catheter when treated with an activating substance in the form of a vapor. The catheter assembly also includes a catheter package forming an interior space divided by a gas permeable, liquid impermeable barrier into a first cavity and a second cavity. The first cavity of the catheter package accommodates the catheter therein and the second cavity accommodates at least a quantity of liquid in its liquid phase therein. The liquid in the second cavity can change phase into a vapor capable of passing from the second cavity, through the barrier, and into the first cavity where the vapor can activate the coating. As a result, the vapor produced when the liquid changes phase causes the coating on the catheter to be activated to thereby produce the low-friction surface on the catheter so it is ready-to-use when it reaches the end user.

8 Claims, 8 Drawing Sheets

(56) References Cited

U.S. PATENT DOCUMENTS

| | | |
|---|---|---|
| 3,291,377 A | 12/1966 | Eggen |
| 3,345,988 A | 10/1967 | Vitello |
| 3,460,529 A | 8/1969 | Leucci |
| 3,556,294 A | 1/1971 | Walck et al. |
| 3,648,704 A | 3/1972 | Jackson .................. 128/349 R |
| 3,651,615 A | 3/1972 | Bohner et al. |
| 3,736,805 A | 6/1973 | Dent |
| 3,854,483 A | 12/1974 | Powers |
| 3,861,395 A | 1/1975 | Taniguchi |
| 3,894,540 A | 7/1975 | Bonner, Jr. |
| 3,898,993 A | 8/1975 | Taniguchi |
| 3,930,580 A | 1/1976 | Bazell et al. |
| 3,934,721 A | 1/1976 | Juster et al. |
| 3,967,728 A | 7/1976 | Gordon et al. |
| 4,026,296 A | 5/1977 | Stoy et al. |
| 4,062,363 A | 12/1977 | Bonner, Jr. |
| 4,119,094 A | 10/1978 | Micklus et al. |
| 4,204,527 A | 5/1980 | Wu et al. |
| 4,230,115 A | 10/1980 | Walz, Jr. et al. |
| 4,248,236 A | 2/1981 | Linder |
| 4,269,310 A | 5/1981 | Uson |
| 4,290,526 A | 9/1981 | Haiss |
| 4,364,478 A | 12/1982 | Tuns |
| 4,379,506 A | 4/1983 | Davidson |
| 4,523,919 A | 6/1985 | Focke et al. |
| 4,652,259 A | 3/1987 | O'Neil |
| 4,754,877 A | 7/1988 | Johansson et al. |
| 4,772,275 A | 9/1988 | Erlich |
| 4,779,727 A | 10/1988 | Taterka et al. |
| 4,811,847 A | 3/1989 | Reif et al. |
| 4,838,429 A | 6/1989 | Fabisiewicz et al. |
| 4,863,016 A | 9/1989 | Fong et al. |
| 4,889,523 A | 12/1989 | Sengewald |
| 4,906,237 A | 3/1990 | Johansson et al. |
| 4,923,061 A | 5/1990 | Trombley, III |
| 4,925,448 A | 5/1990 | Bazaral |
| 4,927,028 A | 5/1990 | Hemm et al. |
| D311,064 S | 10/1990 | Utas-Sjoberg et al. |
| 4,993,555 A | 2/1991 | Hemm |
| 5,001,884 A | 3/1991 | Hanagata et al. |
| 5,038,547 A | 8/1991 | Kai et al. |
| D325,526 S | 4/1992 | Deguchi et al. |
| 5,105,942 A | 4/1992 | van Veen et al. |
| 5,147,341 A | 9/1992 | Starke et al. |
| 5,165,540 A | 11/1992 | Forney |
| 5,180,591 A | 1/1993 | Magruder et al. |
| 5,184,771 A | 2/1993 | Jud et al. |
| 5,203,935 A | 4/1993 | May et al. |
| 5,217,114 A | 6/1993 | Gadberry et al. |
| 5,226,530 A | 7/1993 | Golden |
| 5,242,428 A | 9/1993 | Palestrant |
| 5,322,163 A | 6/1994 | Foos |
| 5,328,848 A | 7/1994 | Fong et al. |
| 5,334,166 A | 8/1994 | Palestrant |
| 5,348,678 A | 9/1994 | Hodam, Jr. et al. |
| 5,356,068 A | 10/1994 | Moreno |
| 5,372,254 A | 12/1994 | Gross |
| 5,416,131 A | 5/1995 | Wolff et al. |
| 5,454,798 A | 10/1995 | Kubalak et al. |
| 5,470,419 A | 11/1995 | Sasaki et al. |
| 5,497,601 A | 3/1996 | Gonzalez |
| 5,501,341 A | 3/1996 | Van Es |
| 5,582,342 A | 12/1996 | Jud |
| 5,688,459 A | 11/1997 | Mao et al. |
| 5,800,412 A | 9/1998 | Zhang et al. |
| 5,836,697 A | 11/1998 | Chiesa |
| 5,848,691 A | 12/1998 | Morris et al. |
| 5,895,374 A | 4/1999 | Rodsten |
| 5,968,069 A | 10/1999 | Dusbabek et al. |
| D416,477 S | 11/1999 | Flint |
| 6,004,305 A | 12/1999 | Hursman et al. |
| 6,053,313 A | 4/2000 | Farrell et al. |
| 6,053,905 A | 4/2000 | Daignault, Jr. et al. |
| 6,059,107 A | 5/2000 | Nøsted et al. |
| 6,065,597 A | 5/2000 | Pettersson et al. |
| 6,098,800 A | 8/2000 | Bennish, Jr. et al. |
| 6,123,712 A | 9/2000 | Di Caprio et al. |
| 6,159,227 A | 12/2000 | Di Caprio et al. |
| 6,185,907 B1 | 2/2001 | Malin et al. |
| 6,228,458 B1 | 5/2001 | Pinchen et al. |
| 6,355,004 B1 | 3/2002 | Pedersen et al. |
| 6,391,010 B1 | 5/2002 | Wilcox |
| 6,403,759 B2 | 6/2002 | Stamler et al. |
| 6,409,717 B1 | 6/2002 | Israelsson et al. |
| 6,415,921 B2 | 7/2002 | Ye et al. |
| 6,457,863 B1 | 10/2002 | Vassallo |
| D467,079 S | 12/2002 | Willows et al. |
| 6,499,278 B2 | 12/2002 | Cronauer et al. |
| 6,506,201 B2 | 1/2003 | Di Caprio et al. |
| 6,578,709 B1 | 6/2003 | Kavanagh et al. |
| 6,602,244 B2 | 8/2003 | Kavanagh et al. |
| 6,634,498 B2 | 10/2003 | Kayerød et al. |
| 6,736,805 B2 | 5/2004 | Israelsson et al. |
| D491,803 S | 6/2004 | Nestenborg |
| 6,745,545 B2 | 6/2004 | Schneider et al. |
| D496,266 S | 9/2004 | Nestenborg |
| D497,205 S | 10/2004 | Kubalak et al. |
| D498,671 S | 11/2004 | Nestenborg et al. |
| D498,672 S | 11/2004 | Nestenborg et al. |
| D499,016 S | 11/2004 | Nestenborg et al. |
| D499,017 S | 11/2004 | Nestenborg et al. |
| D499,335 S | 12/2004 | Nestenborg et al. |
| D499,643 S | 12/2004 | Nestenborg et al. |
| 6,848,574 B1 | 2/2005 | Israelsson et al. |
| 6,848,591 B2 | 2/2005 | Kiel et al. |
| D503,335 S | 3/2005 | Risberg et al. |
| 6,884,206 B2 | 4/2005 | Lasson et al. |
| D505,067 S | 5/2005 | Nestenborg et al. |
| 6,887,230 B2 | 5/2005 | Kubalak et al. |
| 6,974,032 B2 | 12/2005 | Intini et al. |
| 6,996,952 B2 | 2/2006 | Gupta et al. |
| 7,087,048 B2 | 8/2006 | Israelsson et al. |
| 7,311,698 B2 | 12/2007 | Tanghoj et al. |
| 7,334,679 B2 | 2/2008 | Givens, Jr. |
| 7,380,658 B2 | 6/2008 | Murray et al. |
| 7,476,223 B2 | 1/2009 | McBride |
| 7,615,045 B2 | 11/2009 | Israelsson et al. |
| 7,770,726 B2 | 8/2010 | Murray et al. |
| 2001/0001443 A1 | 5/2001 | Kayerod et al. |
| 2001/0054562 A1* | 12/2001 | Pettersson et al. ............ 206/364 |
| 2002/0068180 A1 | 6/2002 | Yang et al. |
| 2003/0008042 A1 | 1/2003 | Khalsa et al. |
| 2003/0018322 A1 | 1/2003 | Tanghoj et al. |
| 2003/0034264 A1 | 2/2003 | Hamai et al. |
| 2003/0035868 A1 | 2/2003 | Coulter et al. |
| 2003/0132128 A1 | 7/2003 | Mazur |
| 2003/0168365 A1 | 9/2003 | Kaern |
| 2003/0174909 A1 | 9/2003 | Parra |
| 2004/0074794 A1 | 4/2004 | Conway et al. |
| 2004/0136623 A1* | 7/2004 | Obara ........................ 383/200 |
| 2004/0142074 A1 | 7/2004 | Hentzel et al. |
| 2004/0153051 A1 | 8/2004 | Israelsson et al. |
| 2005/0003155 A1 | 1/2005 | Huffer |
| 2005/0015076 A1 | 1/2005 | Giebmeyer et al. |
| 2005/0070882 A1 | 3/2005 | McBride |
| 2005/0109648 A1 | 5/2005 | Kerzman et al. |
| 2005/0137582 A1 | 6/2005 | Kull-Osterlin et al. ....... 604/544 |
| 2005/0194276 A1 | 9/2005 | Lubs et al. |
| 2006/0163097 A1 | 7/2006 | Murray et al. |
| 2006/0263404 A1 | 11/2006 | Nielsen et al. |
| 2007/0289887 A1 | 12/2007 | Murray et al. |
| 2008/0260576 A1 | 10/2008 | Bruun et al. |
| 2009/0131917 A1 | 5/2009 | Kavanagh et al. |

FOREIGN PATENT DOCUMENTS

| | | |
|---|---|---|
| CN | 1106744 A | 8/1995 |
| CZ | 197 409 | 8/1979 |
| DE | 2 317 839 A1 | 10/1974 |
| DE | 10 324 012 | 12/2004 |
| DK | 1023/96 C | 8/1965 |
| DK | 1224/96 A | 3/1998 |
| EP | 0 217 771 A1 | 4/1987 |
| EP | 0 440 427 | 8/1991 |
| EP | 0 492 399 | 7/1992 |

| | | |
|---|---|---|
| EP | 0 521 618 | 1/1993 |
| EP | 0 586 324 A1 | 3/1994 |
| EP | 0 677 299 | 10/1995 |
| EP | 0 680 895 A1 | 11/1995 |
| EP | 0 680 896 | 11/1995 |
| EP | 0 685 179 A1 | 12/1995 |
| EP | 0 957 043 | 11/1999 |
| EP | 0 959 021 | 11/1999 |
| EP | 1 095 856 A2 | 5/2001 |
| EP | 1 115 450 A1 | 7/2001 |
| EP | 1 120 355 | 8/2001 |
| EP | 1145729 A1 | 10/2001 |
| EP | 1 262 425 | 12/2002 |
| EP | 1 346 917 | 9/2003 |
| EP | 1 447 345 | 8/2004 |
| EP | 1 642 610 A2 | 4/2006 |
| EP | 1 642 611 A2 | 4/2006 |
| EP | 1 647 298 A2 | 4/2006 |
| EP | 1 809 345 A1 | 7/2007 |
| GB | 1 465 544 | 2/1977 |
| GB | 1 600 963 A | 10/1981 |
| GB | 2 235 680 | 3/1991 |
| GB | 2 284 764 | 6/1995 |
| GB | 2 334 315 A | 8/1999 |
| GB | 2 404 916 | 2/2005 |
| JP | 49-132888 U | 11/1974 |
| JP | 55-012265 A | 1/1980 |
| SE | 9600276-1 | 1/1996 |
| WO | WO-86/06284 A1 | 11/1986 |
| WO | WO-93/03777 A1 | 3/1993 |
| WO | WO-94/06377 A1 | 3/1994 |
| WO | WO-94/16747 A1 | 8/1994 |
| WO | WO-96/30277 A1 | 10/1996 |
| WO | WO-97/26937 A1 | 7/1997 |
| WO | WO-97/39697 A1 | 10/1997 |
| WO | WO-98/06642 | 2/1998 |
| WO | WO-98/11932 A1 | 3/1998 |
| WO | WO-98/19729 A1 | 5/1998 |
| WO | WO-98/58988 A1 | 12/1998 |
| WO | WO-99/42155 | 8/1999 |
| WO | WO-00/16843 A1 | 3/2000 |
| WO | WO-00/30696 A1 | 6/2000 |
| WO | WO-01/52763 A1 | 7/2001 |
| WO | WO-03/008029 A2 | 1/2003 |
| WO | WO-03/064279 | 8/2003 |
| WO | WO-03/093357 A1 | 11/2003 |
| WO | WO-2004/056909 A1 | 7/2004 |
| WO | WO 2005014055 * | 2/2005 |
| WO | WO-2006/037321 A1 | 4/2006 |

OTHER PUBLICATIONS

"LoFric®: The Leading Low Friction, Low Risk Catheter," AstraTech (2006).

"The LoFric Story," AstraTech (2006).

Ikada et al., "Lubricating Polymer Surfaces," Research Center for Biomedical Engineering, Kyoto University, pp. 58-60 (1993).

Kelly et al. "Prolonging the Life of the Hydrophilic-Conted Catheter," British *Journal of Urology*, 79 (Suppl. 4):12 (1997).

Moore, "Intermittent Self-Catheterisation: Research-Based Practice," *British Journal of Nursing*, 4(18):1057 (1995).

O'Neil, "At Last: A System Which Addresses All the Issues of Nosocomial U.T.I. Associated with Catheterization," *Nursing Times*, 33:88-90 (1986).

Tidd et al., "Comparison of Hydrophilic Polymer-Coated Latex, Uncoated Latex and PVC Indwelling Balloon Catheters in the Prevention of Urinary Infection," *British Journal of Urolog*. 48:285-291 (1976).

International Search Report for Application No. PCT/US04/25417, dated Feb. 9, 2005.

International Search Report for Application No. PCT/US07/70783, dated Mar. 31, 2008.

Office Action for U.S. Appl. No. 11/760,545, dated Dec. 29, 2009.
Office Action for U.S. Appl. No. 11/760,545, dated Feb. 25, 2009.
Office Action for U.S. Appl. No. 11/760,545, dated May 21, 2009.
Office Action for U.S. Appl. No. 12/852,959, dated Jan. 7, 2011.
Office Action for U.S. Appl. No. 12/852,959, dated Sep. 14, 2010.
Written Opinion for Application No. PCT/US04/25417, dated Feb. 9, 2005.

Written Opinion for Application No. PCT/US07/70783, dated Mar. 31, 2008.

European Search Report for Application No. EP11150068.2, dated Mar. 7, 2011.

European Search Report for Application No. EP11150060.9, dated Mar. 8, 2011.

Patent Examination Report No. 1 for Australian Patent Application No. 2008/203536 dated Feb. 4, 2013.

* cited by examiner

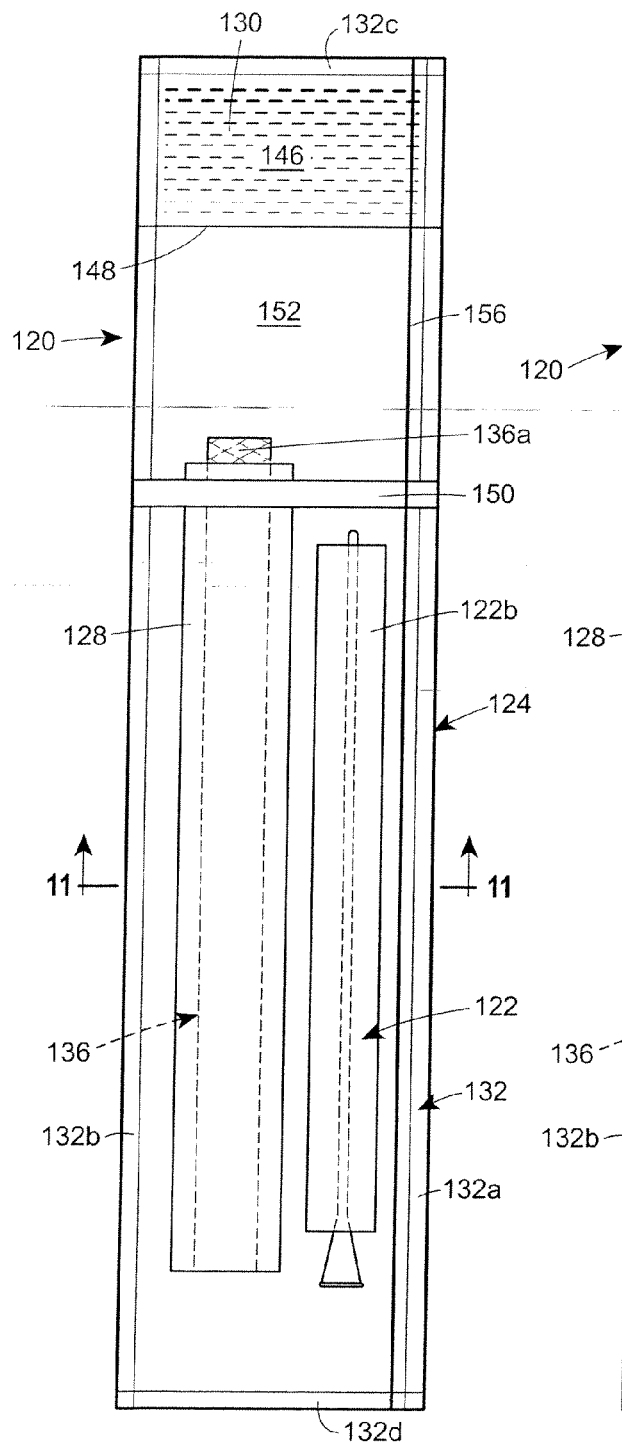
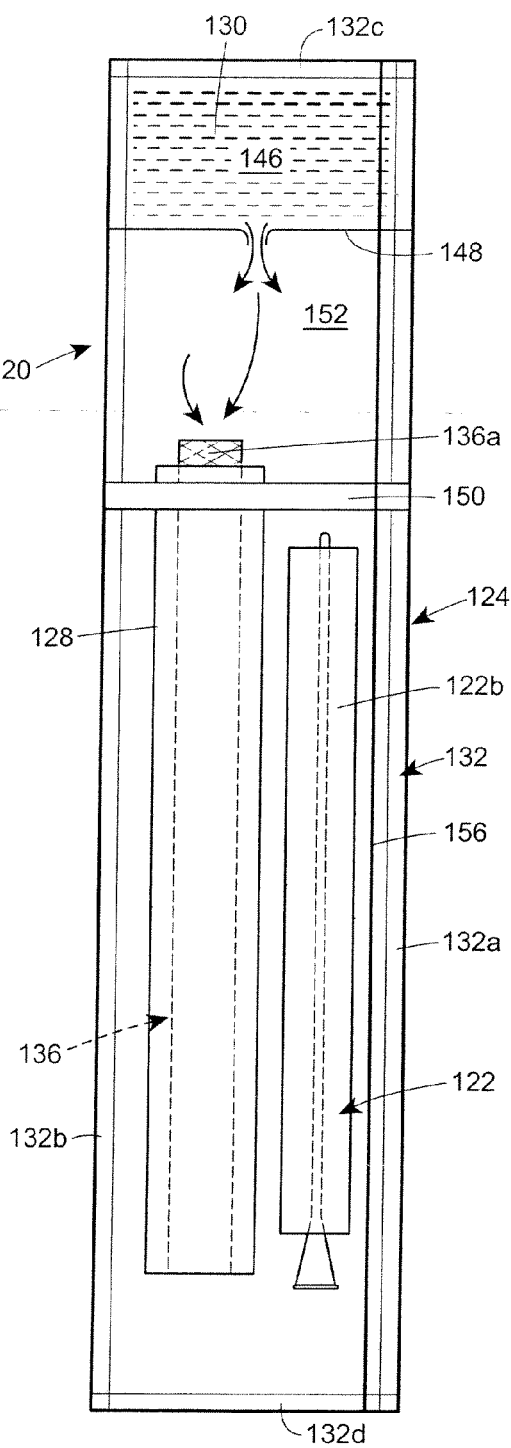

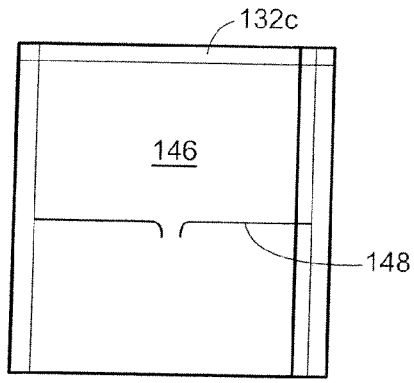
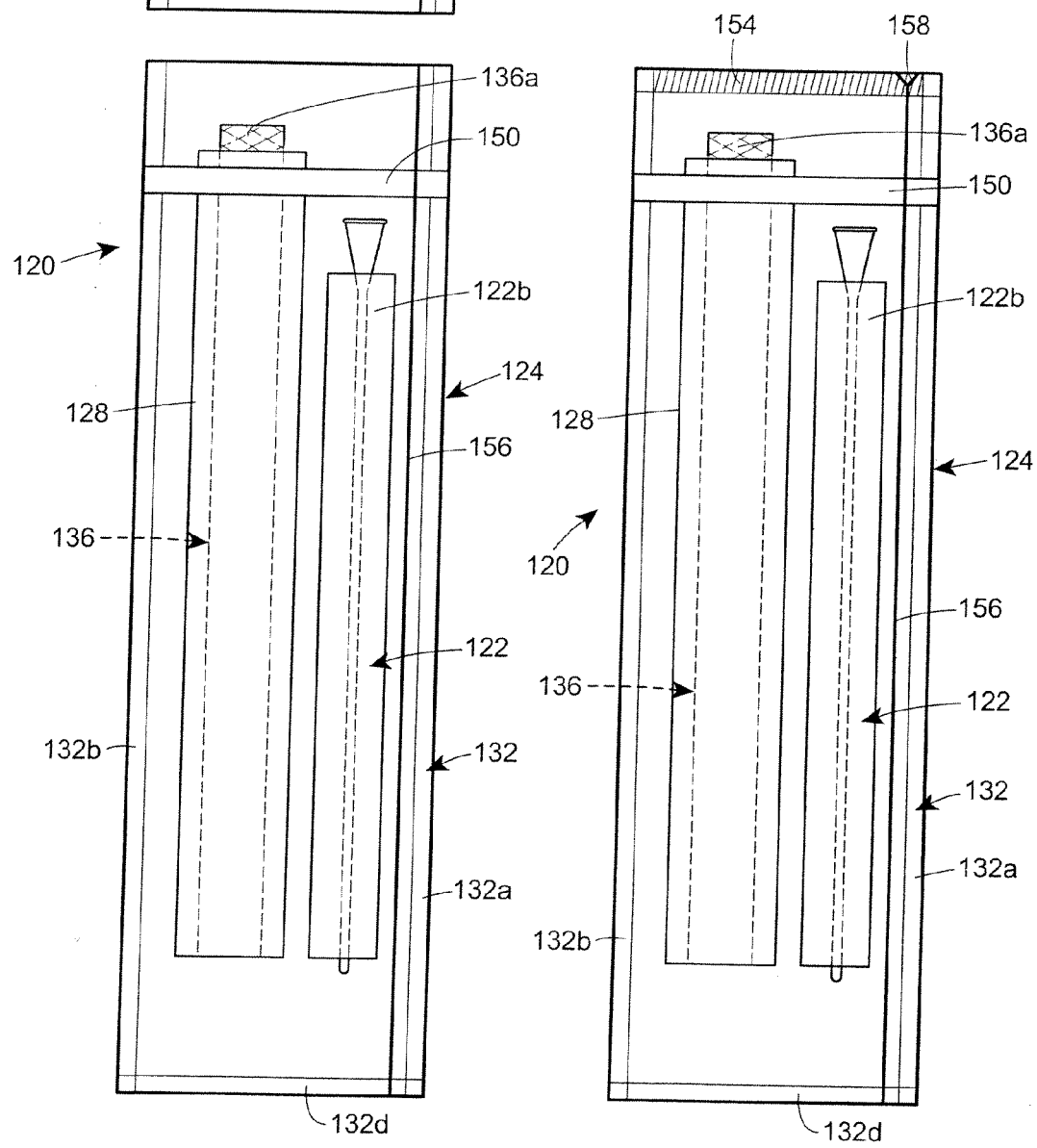

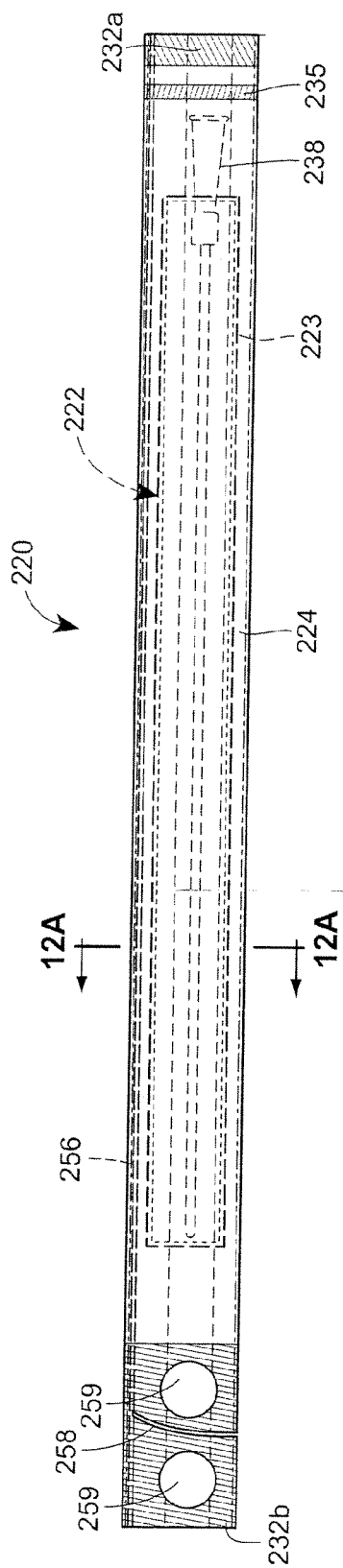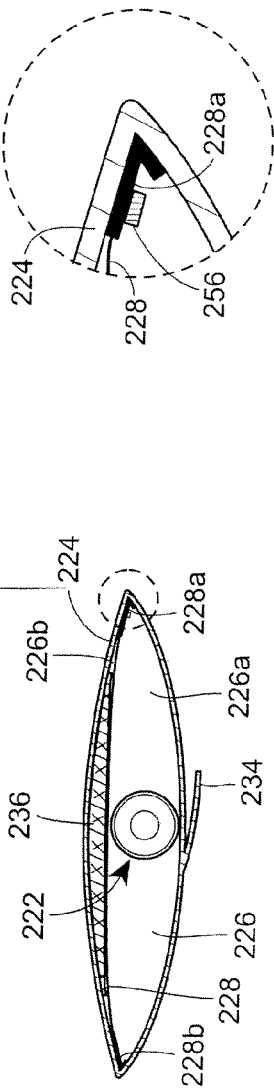

VAPOR HYDRATED CATHETER ASSEMBLY AND METHOD OF MAKING SAME

CROSS REFERENCE TO RELATED APPLICATIONS

This application is a non-provisional application claiming priority to U.S. Provisional Patent Application No. 60/988,920, filed on Nov. 19, 2007.

FIELD OF THE DISCLOSURE

The present disclosure generally relates to catheter assemblies that are delivered to end users in a ready-to-use condition, and more particularly, to such a catheter assembly that is vapor hydrated and a method of making a vapor hydrated catheter assembly.

BACKGROUND OF THE DISCLOSURE

It is generally well known that there are two distinct types of intermittent urinary catheters typically used by those who are able to do so without the assistance of a healthcare professional. These catheters include lubricated catheters which utilize a gel that is applied to the outer surface of the catheter tube prior to insertion into the urethra and hydrophilic catheters wherein a hydrophilic coating on the catheter tube is activated prior to use by treatment with a liquid such as water or saline solution. In the case of hydrophilic catheters, the liquid which is utilized to treat the hydrophilic coating must be provided by the manufacturer if the catheter is to be delivered to an end user in a ready-to-use condition.

As a result, it is necessary for the hydrophilic coating to either be activated at a point in time just prior to placing the catheter in a package or after placing it in a package. The more common approach is to place the hydrophilic coated catheter in a package together with the liquid. In particular, the liquid for activating the hydrophilic coating on the catheter has typically been placed loosely within the package or it has been in a container placed within the package.

With regard to placing the liquid loosely within the package, this has been found to be an undesirable approach because it presents a spill hazard. The loose liquid is typically provided in a reasonably significant quantity to ensure that there will be sufficient liquid remaining through a commercially viable shelf life to maintain the hydrophilic coating in an activated condition. However, since it is necessary to provide a reasonably significant quantity of the liquid to ensure there will be direct contact of the liquid with the hydrophilic coating following assembly, the liquid can easily spill from the package when the package is opened and may thereby wet and/or stain the end user's clothing. In addition, there is a serious technical problem which relates to the condition in which such a ready-to-use hydrophilic catheter must be sterilized.

Specifically, the sterilization process must take place after the catheter and loose liquid have been sealed within the package. Thus, the catheter is sterilized when the hydrophilic coating is wet, i.e., after it already has been activated by the liquid. However, a wet hydrophilic coating may degrade upon sterilization using conventional techniques, e.g., radiation. In particular, the wet hydrophilic coating may detach from the catheter tube resulting in a bumpy, high coefficient of friction surface.

To avoid such sterilization problems, some manufacturers place a liquid container within the package. According to this arrangement, the end user is provided with instructions to rupture or otherwise open the liquid container to permit the liquid to be released within the package so it can activate the hydrophilic coating. The liquid can be provided in a more limited quantity since the user can be instructed to manipulate the package for a period of time to ensure direct contact of the liquid with the hydrophilic coating immediately prior to use. The technical problem of degradation of a wet hydrophilic coating during sterilization is avoided because the liquid is confined to the liquid container during sterilization which means the hydrophilic coating is in a dry state at time of sterilization. However, there are still drawbacks because the catheter is not in a ready-to-use condition when it reaches the end user since the hydrophilic coating requires activation by rupturing/opening the liquid container and manipulating the package.

There is the continuing presence of a spill hazard even though the liquid may be provided in a more limited quantity. The liquid will be contained loosely within the package interior space holding the catheter after the liquid container has been ruptured to release the liquid so it can easily spill on the end user when the package is opened to remove the catheter. In addition, the presence of the liquid can wet the hands of the end user making it more difficult and messy to handle the catheter.

As noted above, hydrophilic coated catheters typically are provided with a thin hydrophilic coating adhered to the outer surface of the catheter for activation by direct contact with a liquid. When the hydrophilic coating is activated by contact with a hydrating liquid such as water, it provides an extremely low coefficient of friction surface. Whether the hydrating liquid is brought into direct contact with the hydrophilic coating by the manufacturer or the end user, it is generally recognized that it takes around 30 seconds to activate the coating.

In all of these existing products, the catheter therefore depends upon direct contact of the liquid swelling medium (e.g., liquid water) with the entirety of the hydrophilic coated catheter surface for a period of time typically recognized as being 30 seconds. Moreover, all of these existing products achieve direct liquid water contact by providing a package for the catheter that permits liquid water to flow freely within the catheter-containing cavity of the package, and permits unobstructed access of the liquid water to the catheter surface for direct contact therewith. Because of the free flow of loose liquid water within the package and unobstructed access to the catheter surface, it is easy to ensure direct contact of the liquid swelling medium with the entire surface of the catheter that has been treated with the hydrophilic coating.

However, it has remained a technical challenge to provide a urinary catheter which has a hydrophilic coating where the catheter meets all of the important criteria for such a product from the perspective of both the manufacturer and the end user, including the ability to sterilize the catheter without degrading the hydrophilic coating due to wetting prior to sterilization or exposing the end user to a spillage hazard from the liquid water which has been placed in direct contact with the hydrophilic coating.

SUMMARY OF THE DISCLOSURE

Accordingly, the present disclosure is generally directed to a catheter assembly comprising a catheter having a hydrophilic coating on at least a part of its length intended to produce a low-friction surface on the catheter when treated with a hydrating substance. The catheter assembly also includes a catheter package forming an interior space divided by a gas permeable, liquid impermeable barrier into first and second distinct and separate cavities. The first cavity accommodates the catheter therein and the second cavity accommodates at least liquid phase water or an aqueous liquid therein. In this regard, the liquid phase water or aqueous liquid therein is capable of changing phase inside the second cavity from a liquid to a vapor which is then available to activate the hydrophilic coating on the catheter.

In its liquid phase, the water or aqueous liquid is confined to the second cavity because of the gas permeable, liquid impermeable barrier dividing the interior space into the two cavities is liquid impermeable. Thus, if the liquid water or aqueous liquid did not undergo a phase change from a liquid to a vapor within the second cavity, the hydrophilic coating on the catheter would not be hydrated. However, after the liquid water or aqueous liquid undergoes a phase change from a liquid to a vapor, the vapor in the second cavity is capable of passing from the second cavity, through the gas permeable, liquid impermeable barrier, into the first cavity.

In the first cavity, the vapor serves as the hydrating substance for the hydrophilic coating, and the vapor is capable of reaching the first cavity because the gas permeable, liquid impermeable barrier dividing the package interior space into two distinct and separate cavities is gas permeable. Therefore, after a phase change, the hydrophilic coating on the catheter will be hydrated by the vapor resulting from the phase change. In other words, the vapor generated by the phase change of the liquid in the second cavity is capable of passing from the second cavity, through the gas permeable, liquid impermeable barrier, into the first cavity to cause the hydrophilic coating on the catheter to be hydrated.

By this arrangement, it is possible to produce the low-friction surface on the catheter so it is in a fully ready-to-use condition when the catheter reaches the end user.

As will be appreciated, the liquid in the second cavity remains a liquid until some or all of it undergoes a phase change to become a vapor. To the extent the liquid changes phase in the second cavity, it will be understood that there will be less liquid remaining in the second cavity, but at no time does liquid ever pass directly from the second cavity into the first cavity because of the gas permeable, liquid impermeable barrier. Accordingly, liquid contained in the second cavity can never directly contact the hydrophilic coating, and it can never directly hydrate the hydrophilic coating; only vapor resulting from a phase change can do that.

While the vapor which passes from the second cavity, through the gas permeable, liquid impermeable barrier, into the first cavity may undergo some condensation within the first cavity, liquid droplets in the first cavity resulting from such condensation will comprise a de minimis amount of liquid far less than would be required to produce liquid hydration of the hydrophilic coating on the catheter.

Preferably, the catheter package forming the interior space is made of a single gas impermeable rectangular sheet, with opposite edges joined by a single longitudinal seal and having an end seal at each of opposite ends thereof. It may alternatively be formed of a gas impermeable material comprised of two confronting rectangular sheets joined by a seal extending entirely about the perimeters of the sheets. Further, the catheter assembly advantageously includes a wicking material within the second cavity. A rupturable container may be provided for selective liquid flow communication with the wicking material.

In one exemplary embodiment, a rupturable container may be provided within the catheter package for selective liquid flow communication with the second cavity in spaced relation to the wicking material. In another exemplary embodiment, the rupturable container may include a rupturable compartment within the catheter package in spaced relation to the wicking material for selective liquid flow communication with the wicking material through a rupturable seal.

From the foregoing, it will be appreciated that the hydrating substance for activating the hydrophilic coating on the urinary catheter comprises water vapor, or vapor phase water. The vapor which is used to activate the hydrophilic coating results from a phase change of water from liquid water to water vapor in the second cavity of the catheter package space.

In another respect, the present disclosure is directed to a method of making a ready-to-use catheter assembly comprising the step of providing a catheter package having an interior space divided by a gas permeable, liquid impermeable barrier into a first cavity and a second cavity. The method also includes the steps of placing a catheter having a hydrophilic coating on at least a part of its length into the first cavity and placing liquid into the catheter package so as to be in liquid isolation relative to the first cavity. Still additionally, the method further includes the step of placing the liquid directly into, or for selective liquid flow communication with, the second cavity of the catheter package and also includes the step of sealing the catheter package such that the catheter is disposed within the first cavity.

In addition, in accordance with another aspect of the disclosure, the method may include the step of delaying distribution or use of the catheter assembly for a period of time sufficient for one or more of several things to occur. In particular, distribution or use may be delayed for a time sufficient for i) the liquid to be placed either directly into, or in selective liquid flow communication with, the second cavity, ii) at least some of the liquid to change phase to vapor within the second cavity, iii) at least some of the vapor to pass from the second cavity, through the gas permeable, liquid impermeable barrier, and into the first cavity, and/or iv) the vapor in the first cavity to hydrate the hydrophilic coating to produce a low-friction surface on the catheter, whereby the catheter assembly is ready-to-use. Furthermore, the method may advantageously include the step of providing the liquid in a rupturable container.

More specifically, the liquid may be provided in a rupturable container which is in communication with the second cavity. The method then may advantageously include the step of providing a wicking material within the second cavity in order to absorb the liquid after the rupturable container has been breached. In this manner, the wicking material can absorb and distribute the liquid so at least a portion of it can thereafter undergo a phase change to change to vapor within the second cavity. The vapor migrates through the vapor permeable, liquid impermeable barrier into the first cavity where it hydrates the hydrophilic coating on the catheter.

As will be appreciated, liquid is always confined to the second cavity because the barrier dividing the interior space of the catheter package into first and second cavities is liquid impermeable. Accordingly, the hydrophilic coating on the catheter in the first cavity cannot be hydrated until at least a portion of the liquid undergoes a phase change to change to vapor. However, once there is vapor present in the second cavity as a result of the phase change, vapor can pass through the barrier into the first cavity to hydrate the hydrophilic coating because the barrier is gas permeable.

One exemplary method includes the steps of forming the catheter package to have a generally elongated rectangular shape and providing the liquid in a rupturable container within the second cavity in spaced relation to one end of the catheter. The method may then advantageously include the step of placing a wicking material in the second cavity to extend longitudinally generally coextensive with the catheter in the first cavity and the wicking material having an end thereof positioned in proximity to the rupturable container. The method may then also advantageously include the step of providing a seal extending inwardly from each side of the catheter package between the catheter and the rupturable container to form a passageway for the liquid to pass to the end of the wicking material.

Another exemplary method includes the steps of forming the catheter package to have a generally elongated rectangular shape and providing the liquid in a rupturable compartment of the catheter package for selective liquid flow communication with the second cavity. The method may then advantageously include the steps of forming the rupturable compartment by providing a rupturable seal and placing a wicking material in the second cavity so as to be longitudinally generally coextensive with the catheter in the first cavity. The method may then also advantageously include the wicking material being positioned in the second cavity for selective liquid flow communication with the rupturable compartment after the rupturable seal is breached and the wicking material having an end in proximity to the rupturable seal.

In the last-mentioned exemplary method, it may further advantageously include the step of forming an intermediate seal across the catheter package between the rupturable seal and the catheter so as to extend across the wicking material to form an intermediate compartment to thereby define a liquid-receiving space.

In both of these exemplary methods, the catheter and the liquid are sterilized after the catheter package has been sealed but before the liquid has been released for absorption by the wicking material. Another feature of the exemplary methods is to sever the catheter package between the catheter and the rupturable container for the liquid after releasing the liquid. Still another feature of the exemplary methods is to thereafter form an end seal for the catheter package so that it is fully sealed for shipment to an end-user in a ready-to-use condition.

A further exemplary method includes the steps of forming the catheter package to have a generally elongated rectangular shape and placing the liquid directly into the second cavity in liquid isolation relative to the catheter. The method may then advantageously include the step of placing a wicking material in the second cavity to extend longitudinally generally coextensive with the catheter in the first cavity. The method may then also advantageously include the step of providing a gas permeable, liquid impermeable barrier within the package interior space to define the first and second cavities and to maintain the liquid out of direct contact with the hydrophilic coated catheter.

In this exemplary method, the catheter and the liquid are sterilized after the catheter package has been sealed. This can be done at the end of the assembly line shortly after the catheter package has been sealed and little or no liquid has vaporized or, by selecting a material for the gas permeable, liquid impermeable barrier having a relatively low gas permeability, sterilization can be done within a few days thereafter. Since, at the time of sterilization, the hydrophilic coating will not have been substantially hydrated by vapor in either instance, the sterilization will not cause the coating to degrade.

Other objects, advantages, and features of the present disclosure will become apparent from a consideration of the following specification taken in conjunction with the accompanying drawings.

BRIEF DESCRIPTION OF THE DRAWINGS

FIG. 7 is a diagrammatic plan view of an alternative embodiment of a vapor hydrated catheter assembly;

FIG. 8 is a diagrammatic plan view of the catheter assembly of FIG. 7 showing one step in the method disclosed herein;

FIG. 9 is a diagrammatic plan view of the catheter assembly of FIG. 7 showing another step in the method disclosed herein;

FIG. 10 is a diagrammatic plan view of the catheter assembly of FIG. 7 showing another step in the method disclosed herein;

FIG. 12 is a diagrammatic plan view of another alternative embodiment of a vapor hydrated catheter assembly;

FIG. 12A is a diagrammatic cross-sectional view of the catheter assembly of FIG. 12 taken generally along the line 12A-12A thereof;

FIG. 12B is an enlarged diagrammatic detail view of the portion of FIG. 12 indicated by a dot-dash circle in FIG. 12, showing the positioning of the heat seal and tear tape;

DETAILED DESCRIPTION

Figure 1:
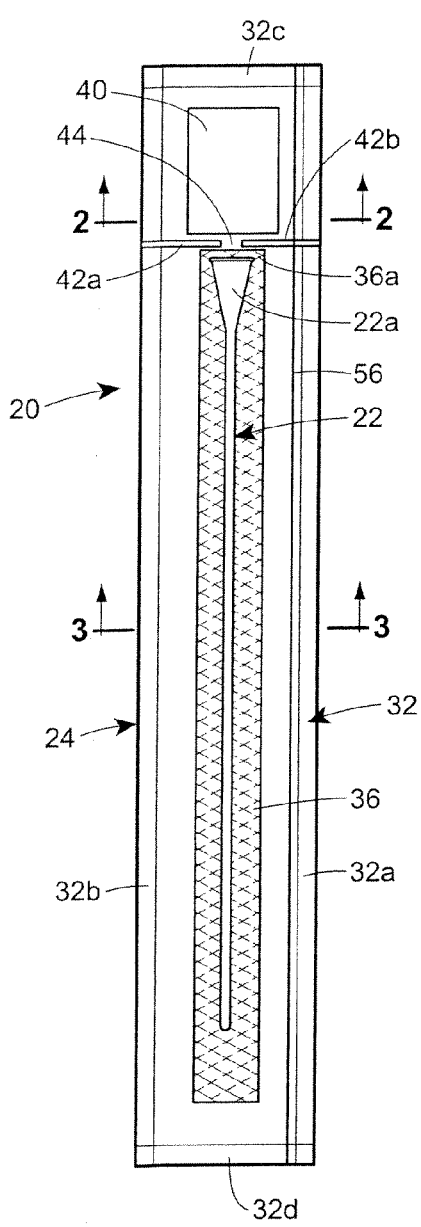
FIG. 1 is a diagrammatic plan view of a vapor hydrated catheter assembly, including a catheter package, constructed in accordance with the present disclosure.

In the illustrations given herein, and with reference first to FIG. 1, the reference numeral 20 designates generally a vapor hydrated catheter assembly in accordance with one aspect of the disclosure. The catheter assembly 20 comprises a urinary catheter generally designated 22 which has a hydrophilic coating on at least a part of its length intended to produce a low-friction surface on the catheter 22 when treated with a hydrating substance. The catheter assembly 20 also includes a catheter package generally designated 24 which forms an interior space 26 (see, also, FIG. 3) divided by a gas permeable, liquid impermeable barrier 28 into a first cavity 26a and a second cavity 26b. The first cavity 26a accommodates the catheter 22 therein and the second cavity 26b accommodates at least a quantity of vapor donating liquid 30 in its liquid phase such as, e.g., liquid phase water therein. The quantity of liquid phase water 30 may contain, for example, pure liquid water, or any suitable aqueous solution. In this regard, the quantity of liquid 30 in its liquid phase is considered to be "vapor donating" because liquid is capable of changing phase inside the second cavity 26b from a liquid to a vapor that can serve as an activating or a hydrating substance. As will be appreciated from FIG. 1, the catheter package 24 is of a generally elongated rectangular shape and includes a rupturable container 40 containing the liquid 30 for selective liquid flow communication with the second cavity 26b.

The liquid 30 is confined within the second cavity 26b because of the liquid impermeable nature of the gas permeable, liquid impermeable barrier 28 which may be configured as a mid-package film or membrane. This film or membrane physically divides the interior space 26 into the two cavities 26a and 26b such that the hydrophilic coating cannot be activated or hydrated until at least a portion of the quantity of vapor donating liquid 30 in its liquid phase undergoes a phase change from a liquid to a vapor. However, after the liquid 30 does undergo a phase change from a liquid to a vapor, the vapor in the second cavity 26b is then capable of passing from the second cavity 26b, through the gas permeable, liquid impermeable barrier 28, and into the first cavity 26a to serve as the activating or hydrating substance.

Figure 2:
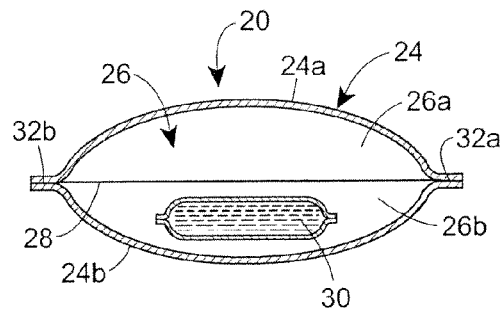
FIG. 2 is a diagrammatic cross-sectional view of the catheter assembly of FIG. 1 taken generally along the lines 2-2 thereof.
Figure 2A:
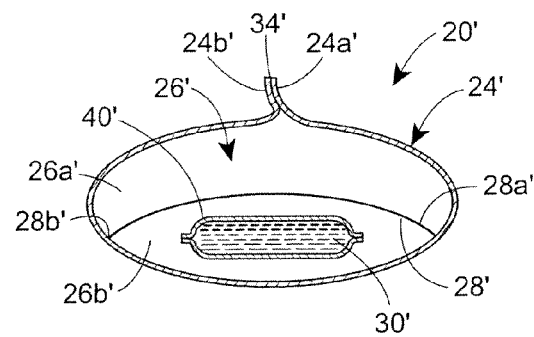
FIG. 2A is a diagrammatic cross-sectional view similar to FIG. 2 but showing an alternative form for the catheter package.
Figure 3:
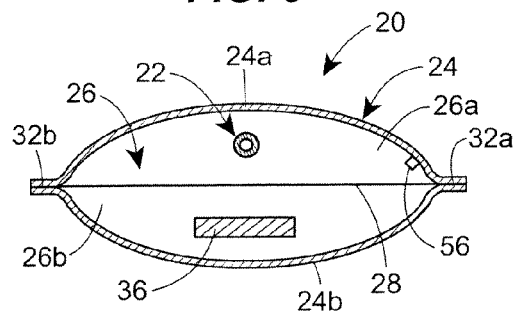
FIG. 3 is a diagrammatic cross-sectional view of the catheter assembly of FIG. 1 taken generally along the lines 3-3 thereof.

In the embodiment illustrated in FIGS. 1 through 3, the catheter package 24 forming the interior space 26 is comprised of two confronting rectangular sheets 24a and 24b of gas impermeable material joined by a seal 32 extending entirely about the perimeters of the sheets 24a and 24b. Alternatively, as will be appreciated from FIGS. 2A and 3A, a catheter package 24' may be formed of a single rectangular sheet of material wrapped about the catheter 22' and the liquid 30' so as to encapsulate them with opposite edges 24a' and 24b' joined by a single longitudinal seal as at 34' and end seals at each of opposite ends thereof. Thus, the only difference between the embodiments shown in FIGS. 2, 3 and FIGS. 2A, 3A is that the latter embodiment has a single longitudinal seal as at 34' because it is formed of a single sheet of material whereas the former embodiment has a pair of longitudinal side seals as at 32a and 32b because it is formed of two sheets of material.

As will be appreciated from the foregoing description, both of the embodiments shown in FIGS. 2 and 2A have end seals such as the end seals 32c and 32d (see FIG. 1) which are provided at each of the opposite ends of the respective packages 24 and 24'.

Figure 3A:
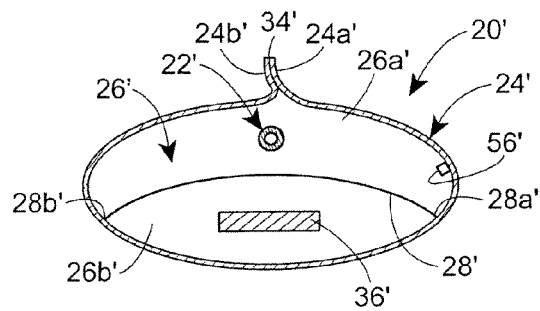
FIG. 3A is a diagrammatic cross-sectional view similar to FIG. 3 but showing an alternative form for the catheter package.
Figure 4:
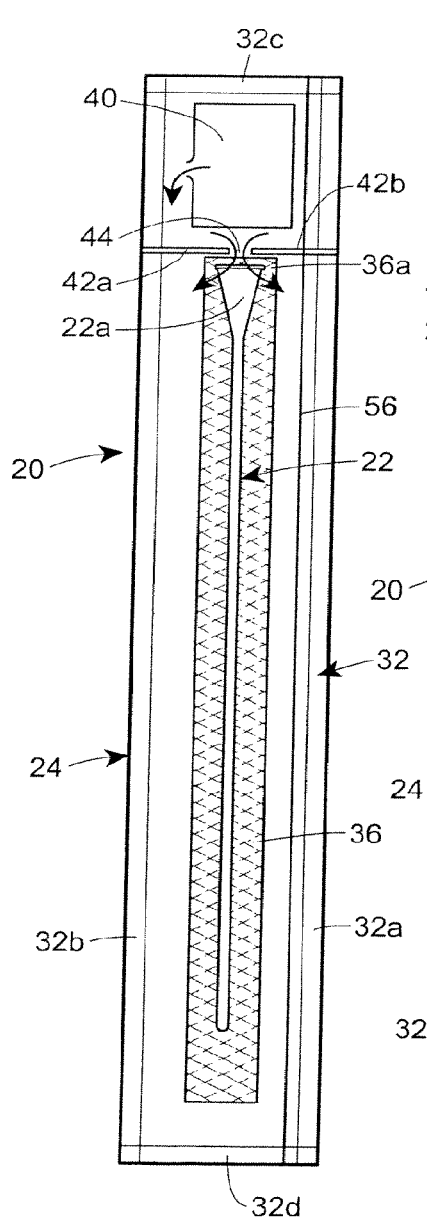
FIG. 4 is a diagrammatic plan view of the catheter assembly of FIG. 1 showing one step in the method disclosed herein.
Figure 5:
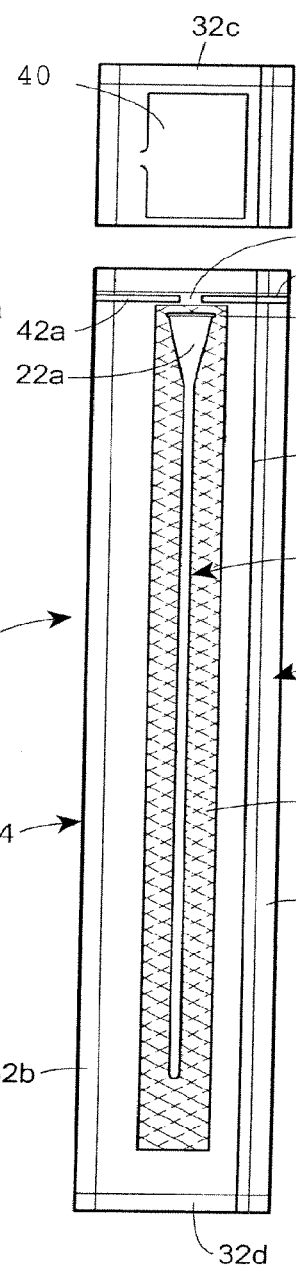
FIG. 5 is a diagrammatic plan view of the catheter assembly of FIG. 1 showing another step in the method disclosed herein.

Referring to FIGS. 1, 3, and 3A, it will be seen that the catheter assemblies 20, 20' include a wicking material 36, 36' within the second cavities 26b, 26b' of the interior spaces 26, 26' for selective liquid flow communication with the rupturable container 40 for the liquid 30, 30', to absorb the liquid 30, 30' when the rupturable container 40 is breached. It will again be appreciated that the only difference between the embodiments shown in FIGS. 3 and 3A is the difference in the catheter packages 24 and 24' as described in detail above. In other words, FIGS. 3 and 3A illustrate, respectively, the wicking material 36 within the second cavity 26b in a catheter package 24 formed of two sheets of material (FIG. 3) and the wicking material 36' within the second cavity 26b' in a catheter package 24' formed of a single sheet of material (FIG. 3A).

The wicking material 36 within the second cavity 26b extends longitudinally so as to be generally coextensive with the catheter 22 in the first cavity 26a. An end 36a of the wicking material 36 is preferably positioned in spaced relation but in proximity to the rupturable container 40. The catheter package 24 includes seals 42a and 42b extending inwardly from each side of the package between the catheter 22 and the rupturable container 40 to form a passageway as at 44 for the liquid 30 to pass from the rupturable container 40, after it has ruptured, to the end 36a of the wicking material 36.

While not specifically shown, it will be appreciated that the structural features as well as the details of construction of the catheter assembly 20' in the embodiment of FIGS. 2A and 3A are designated by a "prime" symbol and are essentially identical to those described above in connection with the catheter assembly 20, except where noted otherwise.

Referring now to FIGS. 7 through 11, an alternative embodiment of a catheter assembly 120 is illustrated which includes a catheter generally designated 122 having a hydrophilic coating on at least a part of its length intended to produce a low-friction surface on the catheter 122 when treated with a hydrating substance. The catheter assembly 120 also includes a catheter package generally designated 124 which is formed of a gas impermeable material to have an interior space 126 divided by a gas permeable, liquid impermeable barrier 128 into first and second cavities 126a and 126b. The first cavity 126a accommodates the catheter 122 therein and the second cavity 126b accommodates a wicking material 136 for communication with a liquid 130.

The liquid 130 is within a rupturable compartment 146 within the catheter package 124 in spaced relation to the wicking material 136 for selective liquid flow communication with the wicking material 136 through a rupturable seal 148. The wicking material 136 is within the second cavity 126b of the interior space 126 for selective liquid flow communication with the rupturable compartment 146 within the catheter package 124 containing the liquid 130 after the rupturable seal 148 is breached. The liquid 130 absorbed by the wicking material 136 is capable of undergoing a phase change from a liquid to a vapor. After the liquid 130 undergoes a phase change, the vapor resulting from the phase change passes from the second cavity 126b, through the gas permeable, liquid impermeable barrier 128, and into the first cavity 126a to hydrate the hydrophilic coating to produce the low-friction surface on the catheter 122.

As with the embodiment illustrated in FIGS. 1 and 2, the catheter package 124 is of a generally elongated rectangular shape, but has a rupturable compartment 146 containing the liquid 30 rather than a rupturable container such as 40 in FIG. 1. The rupturable compartment 146 is disposed for selective liquid flow communication with the second cavity 126b.

With regard to the respective embodiments of FIGS. 1 and 2 and FIGS. 7 and 11, the packages 24 and 124 are comprised of two confronting rectangular sheets 24a, 24b and 124a, 124b, respectively, which overlie one another and are joined together by seals 32 and 132, respectively, which include longitudinal side seals 32a, 32b and 132a, 132b, respectively, as well as end seals 32c, 32d and 132c, 132d, respectively. The gas permeable, liquid impermeable barriers 28 and 128 serve to divide the interior spaces 26 and 126, respectively, into first cavities 26a, 126a, respectively, and second cavities 26b, 126b, respectively, as shown.

Figure 11:
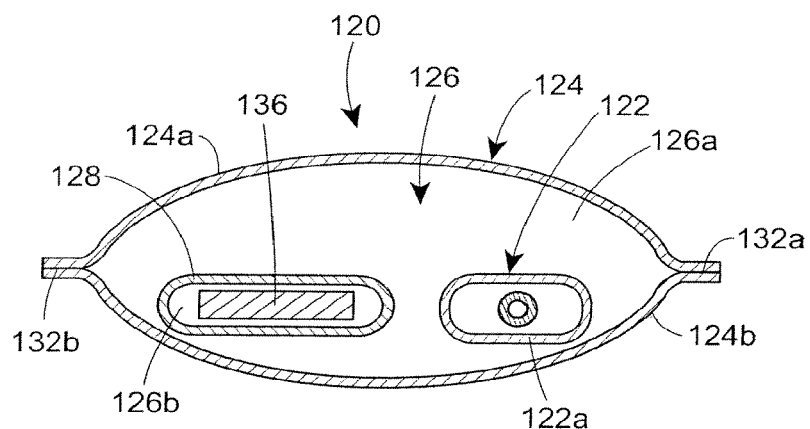
FIG. 11 is a diagrammatic cross-sectional view of the catheter assembly of FIG. 7 taken generally along the lines 11-11 thereof.

However, the gas permeable, liquid impermeable barrier 128 in the embodiment of FIGS. 7 and 11 is formed quite differently from the gas permeable, liquid impermeable barrier 28 in the embodiment of FIGS. 1 and 2 in that the former comprises a gas permeable, liquid impermeable sleeve, rather than a mid-package film or membrane, which holds and confines the wicking material 136 so as to be maintained in liquid isolation from the catheter 122 within the interior space 126 of the package 124.

Figure 11A:
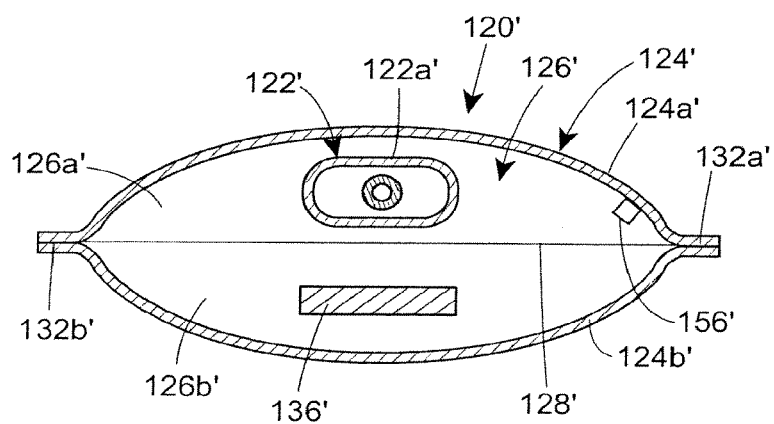
FIG. 11A is a diagrammatic cross-sectional view similar to FIG. 11 but showing an alternative form of liquid barrier in the catheter package.

Referring to FIG. 11A, it is possible as an alternative to utilize a gas permeable, liquid impermeable barrier 128' formed in a substantially similar manner to the gas permeable, liquid impermeable barrier 28 in FIGS. 1 and 2 such that the gas permeable, liquid impermeable barrier 128' will extend entirely through the interior space 126' and be captured by the longitudinal side seals such as 132a', 132b' and at least one of the end seals such as 132d so as to be sealed with the confronting rectangular sheets 124a', 124b'.

When this alternative embodiment is utilized, the gas permeable, liquid impermeable barrier 128' will be seen to comprise a mid-package film or membrane which cooperates with the rectangular sheets 124a', 124b' and the various seals to divide the interior space 126' into a first cavity 126a' and a second cavity 126b' such that the catheter 122' is accommodated in the first cavity 126a' of the interior space 126' and the wicking material 136' is disposed within the second cavity 126b'. As before, the liquid 130 is in a separate compartment such as the rupturable compartment 146 which is in liquid flow communication with the second cavity 126b' and, thus, with the wicking material 136' when the rupturable seal 148 is breached so that the liquid 130 can reach the end 136a of the wicking material 136' (as seen in FIGS. 7 through 10) to be wicked or drawn therein.

In both of the embodiments which are illustrated in FIGS. 11 and 11A, the wicking material 136 and 136' within the respective second cavities 126b and 126b' extend longitudinally generally coextensive with the respective catheters 122 and 122' so as to have an end such as 136a thereof which is positioned in spaced relation, but in proximity to, the rupturable compartment 146 containing the liquid 130. Furthermore, in both of the embodiments which are illustrated in FIGS. 11 and 11A, there is a rupturable seal 148 (see FIGS. 7 through 9) defining one boundary of the rupturable compartment 146 for the liquid 130, and there is also an intermediate seal 150 disposed between the rupturable seal 148 and the respective catheters 122 and 122' extending across the respective wicking materials 136 and 136' to define an intermediate compartment such as 152.

With regard to the embodiment illustrated in FIG. 11A, the intermediate seal 150 will be understood to capture the end of the gas permeable, liquid impermeable barrier 128' opposite the end thereof which is captured by the end seal 132d. In other words, it will be understood that the gas permeable, liquid impermeable barrier 128' in FIG. 11A is captured entirely about its perimeter by the respective side seals 132a' and 132b' 124' as well as an end seal 132d and the intermediate seal 150 (FIG. 7). As a result, it will be appreciated that only the end portion 136a of the wicking material 136' will extend outwardly of the interior space 126' so as to be in the intermediate compartment 152 (FIG. 7).

When a single sheet of material is used to form a package such as 24' in FIGS. 2A and 3A, the edges of the gas permeable, liquid impermeable barrier 28' will not be captured by opposed side seals such as those shown in FIGS. 2 and 3. Instead, opposite side edges 28a' and 28b' of the gas permeable, liquid impermeable barrier such as 28' will be secured to the inner surface of the package 24'. While not specifically shown, it will be appreciated that the embodiment shown in FIG. 11A can also be constructed of a single sheet of material to form the package 124' in substantially the same manner.

As shown in FIGS. 7 and 11, the catheter package 120 is formed such that the intermediate compartment 152 is between the first and second cavities 126a and 126b which accommodate the catheter 122 and the wicking material 136, on the one hand, and the rupturable compartment 146 which is provided for the liquid 130, on the other hand, for a reason which will be appreciated from the description of the disclosed method below. The intermediate compartment 152 will be seen to extend between the wicking material 136 and the rupturable seal 148 of the rupturable compartment 146 to define a liquid-receiving space after the rupturable seal 148 has been breached to release the liquid 130. Furthermore, and as will be appreciated by referring to FIGS. 8 and 11, the wicking material 136 will be seen to have the end portion 136a which extends from the second cavity 126b through the intermediate seal 150 and into the intermediate compartment 152 whereby it is able to wick and absorb the liquid 130 from the intermediate compartment 152 into the second cavity 126b.

Still referring to FIGS. 7 and 11, the intermediate seal 150 cooperates with the sleeve-like gas permeable, liquid impermeable barrier 128 so as to confine liquid drawn into the wicking material 136 to the second cavity 126b and thereby keep liquid from entering the first cavity 126a. While not essential to the present disclosure, the catheter 122 shown in FIG. 7 can also be provided with a "no-touch" gas permeable, liquid impermeable sleeve 122a through which vapor in the first cavity 126a can pass in order to hydrate the hydrophilic coating on the catheter 122. The "no-touch" gas permeable, liquid impermeable sleeve 122a permits the end user to manipulate the catheter 122 without touching the surface of the catheter 122. This feature reduces contamination risk and makes the catheter 122 easier to handle for the end user. The "no touch" sleeve can be a complete barrier to microorganisms, including viruses, thus providing significant protection for the user. This is possible only if the "no touch" sleeve is made of a material that is liquid impermeable, such as a monolithic polymer film.

The sleeve 122a may advantageously cover the entire hydrophilic coated portion of the catheter to make it possible for the end user to avoid making contact with the portion of the catheter which is intended to be inserted into the urethra to thereby prevent or limit the possibility of urinary tract infections.

In contrast to the embodiment illustrated in FIGS. 7 and 11, the wicking material 136' in FIG. 11A can be loosely positioned within the second cavity 126b'. However, it will be appreciated that in the FIG. 11A embodiment there will also be an intermediate seal such as 150 in FIG. 7. In this case, the intermediate seal 150 will cooperate directly with the wicking material 136' and the gas permeable, liquid impermeable barrier 128' to confine liquid drawn into the wicking material to the second cavity 126b'.

More specifically, the resulting product will resemble FIG. 7 with the sleeve-like gas permeable, liquid impermeable barrier 128 removed and the mid-package film or membrane gas permeable, liquid impermeable barrier 128' taking its place to physically separate the catheter 122' and the wicking material 136' into the first and second cavities 126a' and 126b' shown in FIG. 11A. Considering FIGS. 7 and 11A together, it will be appreciated that this is accomplished by having the side seals 132a' and 132b', an end seal such as 132d and an intermediate seal such as 150 cooperate with the rectangular sheets 124a', 124b' and the gas permeable, liquid impermeable barrier 128' to form the first and second cavities 126a' and 126b'. Further, it will also be appreciated that the wicking material 136' will have an end 136a' thereof extend beyond the intermediate seal 150 into an intermediate compartment 152 where it can wick and absorb the liquid 130.

In all of the foregoing embodiments, both the catheter 22, 22', 122, 122' and the wicking material 36, 36', 136, 136' are disposed in a catheter package 24, 24', 124, 124' of a generally elongated rectangular shape. The catheter 22, 22', 122, 122' and at least a major portion of the wicking material 36, 36', 136, 136' are also disposed between seals 42a and 42b, or between intermediate seal 150 and the end seal 32d or 132d. The foregoing features will be appreciated by referring to FIGS. 1, 3, 3A, 7, 11, 11A, and the reason they are located as described will be appreciated from the description of the disclosed method.

Figure 6:
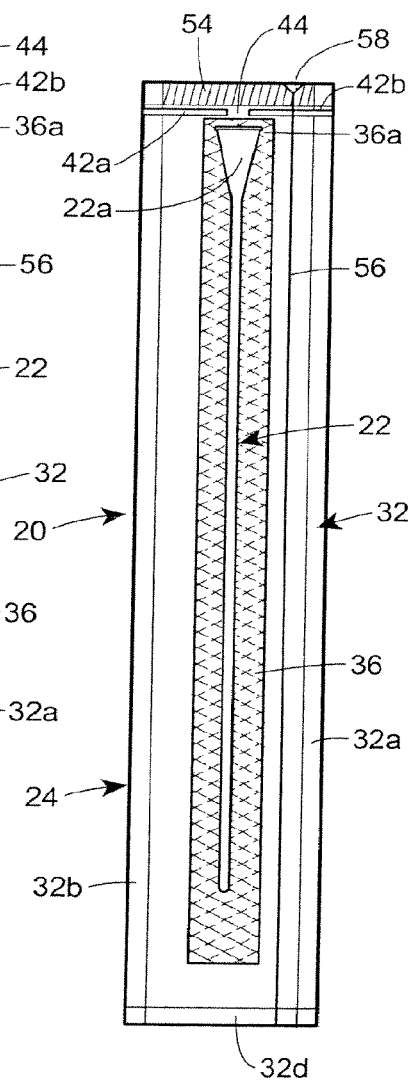
FIG. 6 is a diagrammatic plan view of the catheter assembly of FIG. 1 showing another step in the method disclosed herein.

Before describing the method, it will also be noted in all embodiments that each of the respective catheter packages 24, 24', 124, 124' has a tear tape 56, 56', 156, 156' which may be adhesively affixed to the inner surface of the sheet material forming the catheter package 24, 24', 124, 124'. The tear tape 56, 56', 156, 156' is affixed such that it is positioned along one side edge of the catheter package 24, 24', 124, 124' within the first sealed cavity 26a, 26a', 126a, 126a'. In addition, each of the respective catheter packages 24, 24', 124, 124' may include a v-notch such as 58 (FIG. 6) and 158 (FIG. 10) which extends a short distance into the end seal 54, 154 to facilitate opening the package by causing it to tear along the tear tape 56, 56', 156, 156'.

When the end user opens the package by using the tear tape 56, 56', 156, 156', the tear tape 56, 56', 156, 156' will be understood to cause the catheter package 24, 24', 124, 124' to tear along it to thereby cause the catheter package 24, 24', 124, 124' to open along an intended opening line for access to the catheter 22, 22', 122, 122' in the first sealed cavity 26a, 26a', 126a, 126a' without opening the second sealed cavity 26b, 26b', 126b, 126b'. The tear tape 56, 56', 156, 156' thus extends within the first sealed cavity 26a, 26a', 126a, 126a' in a desired direction relative to the catheter 22, 22', 122, 122' to cause the package 24, 24', 124, 124' to open along the intended opening line in a manner facilitating removal of the catheter from the package for use without opening the second sealed cavity 26b, 26b', 126b, 126b'. Thus, residual liquid still present in the second cavity 26b, 26b', 126b, 126b' that has not changed phase into vapor is safely confined to the second cavity 26b, 26b', 126b, 126b' and cannot spill on the end user. The tear tape 56, 56', 156, 156' can advantageously be adhesively or otherwise affixed to an inner surface of the catheter package 24, 24', 124, 124' within the first sealed cavity 26a, 26a', 126a, 126a' so as to extend generally from one end of the catheter package to the other end thereof in a manner whereby it will be generally parallel to the catheter 22, 22', 122, 122'.

When the end user opens the catheter package 24, 24', 124, 124', less of the original liquid 30, 130 will be present in the second cavity 26b, 26b', 126b, 126b' as compared to the time of manufacture, because some of it will have changed phase to a vapor. However, for the liquid 30, 130 which does remain, it is safely confined in the second cavity 26b, 26b', 126b, 126b'. By taking advantage of vapor hydration of the hydrophilic coating and isolating the liquid 30, 130 in a cavity that remains sealed even after removing the catheter 22, 22', 122, 122' from the catheter package 24, 24', 124, 124', there is no possibility of spillage.

While the vapor which passes from the second cavity 26b, 26b', 126b, 126b', through the gas permeable, liquid impermeable barrier 28, 28', 128, 128', into the first cavity 26a, 26a', 126a, 126a' may undergo some observable condensation within the first cavity, the liquid droplets which may be found in the first cavity resulting from such condensation will comprise, at most, a de minimis amount of liquid which will be far less than what would be required to produce liquid hydration of the hydrophilic coating on the catheter 22, 22', 122, 122' and far less than what could possibly cause a spillage hazard. Some of this condensation may occur at a water activity below unity, due to the presence of surfaces and small spaces within the package, and may not be thermodynamically driven to enter the hydrophilic coating. In any event, the small liquid water droplets formed by condensation will not be capable of fully hydrating the coating and making the product ready to use by the conventional fast liquid activation.

It is possible to control the time for completing the hydration of the hydrophilic coating by selecting the degree of vapor permeability of the gas permeable, liquid impermeable barrier and, if used, the degree of vapor permeability of the "no-touch" catheter sleeve.

As also previously mentioned, the hydrating substance for activating the hydrophilic coating on the urinary catheter comprises water vapor (vapor phase water). The water vapor which is used to activate the hydrophilic coating is at least in part from water that previously had been liquid water resident in the second cavity. Thus, some of the quantity of water placed within the catheter package in its liquid phase may change phase to vapor and thus continuously replace water vapor lost from the gas phase as it enters and activates the hydrophilic coating.

EXAMPLE

A hydrophilic coating based on cross-linked polyvinylpyrrolidone was created on the surface of a PVC tube. A CaCO3 filled polyethylene film (#728 from RKW, Belgium) was used as the gas permeable, liquid impermeable barrier separating the interior space formed by the catheter package into first and second cavities and a polyurethane film, designated as PT9300 from Deerfield Urethane, Deerfield, Mass., was used as the "no-touch" sleeve surrounding the coated tube. A wicking material made from an air laid hydrophilic polyester fabric with plastic netting laminated to both sides (available from DelStar Technologies Inc., Middleton Del.—designated as 4.5NPET-EE/EE) was placed in the second cavity, and wetted with more liquid phase water than required to provide sufficient vapor phase water for activating the coating. Then the second cavity was formed by sealing the polyethylene film to the package wall with the wicking material disposed therebetween. After forming the second cavity, the coated tube was placed onto the film outside the second cavity and the catheter package was sealed to form the first cavity. 96 hours after sealing the catheter package, the product was radiation sterilized.

After radiation sterilization, and after aging at room temperature for six weeks post package sealing, the coated tube was lubricious, and coefficient of friction testing indicated that the coated tube was now in a highly lubricious, ready to use state, with a fully functional, hydrated, lubricious coating.

Referring to FIGS. 12 and 12A, another alternative embodiment of catheter assembly 220 is illustrated which includes a catheter generally designated 222 having a hydrophilic coating on at least a part of its length intended to produce a low-friction surface on the catheter 222 when treated with a hydrating substance. The catheter assembly 220 also includes a catheter package 224 which is formed of a gas impermeable material to have an interior space 226 divided by a gas permeable, liquid impermeable barrier 228 into first and second cavities 226a and 226b. The first cavity 226a accommodates the catheter 222 therein and the second cavity 226b accommodates a wicking material 236 that has been wetted with a liquid. The liquid is placed directly on the wicking material 236 at the time of manufacture of the catheter assembly 220. The wicking material 236 is within the second cavity 226b where at least some of the liquid can undergo a phase change from a liquid to a vapor. After the phase change, the vapor resulting from the phase change passes from the second cavity 226b, through the gas permeable, liquid impermeable barrier 228, and into the first cavity 226a, where it is capable of hydrating the hydrophilic coating to produce the low-friction surface on the catheter 222.

The liquid is confined to the second cavity 226b because of the liquid impermeable nature of the gas permeable, liquid impermeable barrier 228 which comprises a mid-package film or membrane. This film or membrane physically divides the interior space 226 into the two cavities 226a and 226b such that the hydrophilic coating cannot be hydrated until the liquid undergoes a phase change from a liquid to a vapor. However, after the liquid changes phase from a liquid to a vapor, the vapor in the second cavity 226b is then capable of passing from the second cavity 226b, through the gas permeable, liquid impermeable barrier 228, and into the first cavity 226a to serve as the hydrating substance. In particular, the vapor resulting from the phase change of the liquid passes into the first cavity 226a where it hydrates the hydrophilic coating to produce the low-friction surface on the catheter 222.

As an alternative, the gas permeable, liquid impermeable barrier 228 shown as a mid-package film or membrane in FIGS. 12, 12A and 12B can instead be formed into an entirely enclosed container defining the second cavity 226b. This container can then be placed within the interior space 226, either loosely or tacked in place. Moreover, the container can either have the wicking material 236 wetted with a quantity of liquid within the second cavity 226b or, alternatively, a quantity of liquid can simply be placed loosely within the second cavity 226b defined by the container.

Preferably, this alternative has the container formed as an elongated tube that will be substantially coextensive with at least the portion of the catheter 222 having the hydrophilic coating thereon so that as at least some of the quantity of liquid can change phase into a vapor and pass through the gas permeable, liquid impermeable barrier 228 from the second cavity 226b defined by the container into the first cavity containing the catheter 222 to activate the hydrophilic coating.

As with the embodiment of FIGS. 2A and 3A, the catheter package 224 may be formed of a single rectangular sheet of material wrapped about the wicking material 236 which has been wetted with a liquid, and about the catheter 222 to encapsulate them with opposite edges joined by a single longitudinal seal as at 234 and end seals 232a and 232b at opposite ends thereof. Thus, in the same manner as the embodiment of FIGS. 2A, 3A the catheter package 224 shown in FIGS. 12, 12A also has a single longitudinal seal as at 234 because it is also formed of a single sheet of material. As will further be appreciated from the foregoing description together with FIGS. 12, 12A, the catheter package 224 has the gas permeable, liquid impermeable barrier 228 sealed to the inner surface of the single sheet of material as at 228a, 228b (see FIGS. 12A and 12B) and has end seals 232a, 232b (see FIG. 12) at each of the opposite ends of the package 224.

As described in connection with the earlier embodiments, it will be noted in FIGS. 12, 12A and 12B that the catheter package 224 has a tear tape 256 which may be adhesively affixed to the inner surface of the sheet material which serves to form the catheter package 224. The tear tape 256 is affixed such that it is positioned along one side edge of the catheter package 224 within the first sealed cavity 226a. In addition, the catheter package 224 has a slit 258 and finger openings 259 (FIG. 12). The slit 258 may extend through the end seal 232b to a point near the tear tape 256 to facilitate opening the catheter package 224 by causing it to tear along the tear tape 256.

As will be appreciated, when the end user opens the catheter package 224 by using the tear tape 256, it provides access to the catheter 222 because it opens the first sealed cavity 226a in which the catheter 222 is accommodated. Further, even after the catheter package 224 is opened in this manner, the second cavity 226b remains completely sealed. Thus, residual liquid still present in the second sealed cavity 226b of the catheter package 224 that has not changed phase to vapor is safely confined to the second cavity 226b and cannot spill on the end user.

The tear tape 256 will be understood to cause the catheter package 224 to tear along it to thereby cause the catheter package 224 to open along an intended opening line for access to the catheter 222 in the first sealed cavity 226a without opening the second sealed cavity 226b. The tear tape 256 thus extends within the first sealed cavity 226a in a desired direction relative to the catheter 222 to cause the catheter package 224 to open along the intended opening line in a manner facilitating removal of the catheter 222 from the package for use without opening the second sealed cavity 226b. The tear tape 256 can advantageously be adhesively or otherwise affixed to an inner surface of the catheter package 224 within the first sealed cavity 226a so as to extend generally from one end of the catheter package 224 to the other end thereof in a manner whereby it will be generally parallel to the catheter 222.

When the end user opens the catheter package 224, less of the original liquid will be present in the second cavity 226b as compared to the time of manufacture, because some of it will have changed phase to vapor. However, for remaining liquid, it is safely confined in the second cavity 226b. By taking advantage of vapor hydration of the hydrophilic coating and isolating the liquid in a sealed cavity even after removing the catheter from the package, there is no possibility of spillage.

While the vapor which passes from the second cavity 226b, through the gas permeable, liquid impermeable barrier 228, into the first cavity 226a may undergo some observable condensation within the first cavity, the liquid droplets which may be found in the first cavity resulting from such condensation will comprise, at most, a de minimis amount of liquid which will be far less than what would be required to produce liquid hydration of the hydrophilic coating on the catheter 222 and far less than what could possibly cause a spillage hazard.

Figure 13:
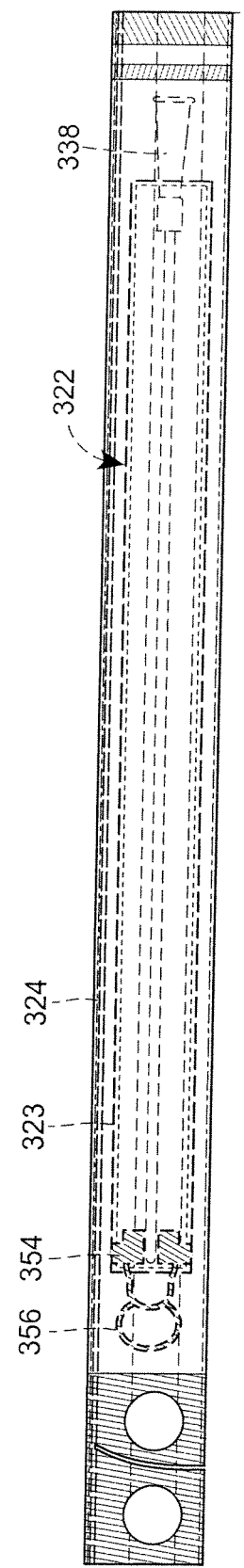
FIG. 13 is a diagrammatic plan view of still another alternative embodiment of a vapor hydrated catheter assembly.

Still referring to FIGS. 12 and 12A, it will be appreciated that the gas permeable, liquid impermeable barrier 228 will run the full length of the package 224 so that opposite ends thereof are captured within the heat seals 232a and 232b. The heat seals 228a and 228b cooperate with the heat seals 232a and 232b to complete the heat sealing of the gas permeable, liquid impermeable barrier 228 entirely about its perimeter to thereby form the liquid tight second cavity 226b. The package 224 may also have a heat seal such as 235 which serves to prevent possible backflow of liquid during the manufacturing assembly process until such time as the heat seal 232a has been formed Referring to FIG. 13, it will be seen that the package 324 is structurally identical to the package 224 in FIGS. 12, 12A and 12B. The embodiments shown in FIG. 12 and in FIG. 13 each include a "no-touch" sleeve 223, 323, respectively, which extends along the hydrophilic coated catheter 222, 322 so as to cover substantially the entire insertable portion of the catheter 222, 322. However, the package 324 in FIG. 13 is shown with a catheter 322 having an insertion tip 354 at one end thereof and also having a "no-touch" sleeve 323 that may be attached to the insertion tip 354. The "no-touch" sleeve 223, 323 may be alternatively or additionally attached at or near the funnel end of the catheter 222, 322, i.e., it may be attached either at a point along the distal half of the catheter 222, 322 (not shown) or directly to the funnel/connector 238, 338 as shown in FIGS. 12 and 13. Alternatively, the "no-touch sleeve 223, 323 may be unattached to the catheter 222, 322. In FIG. 13, the catheter 322 also includes a protective cap 356 covering the insertion tip 354 to be removed for using the catheter 322.

Figure 14:
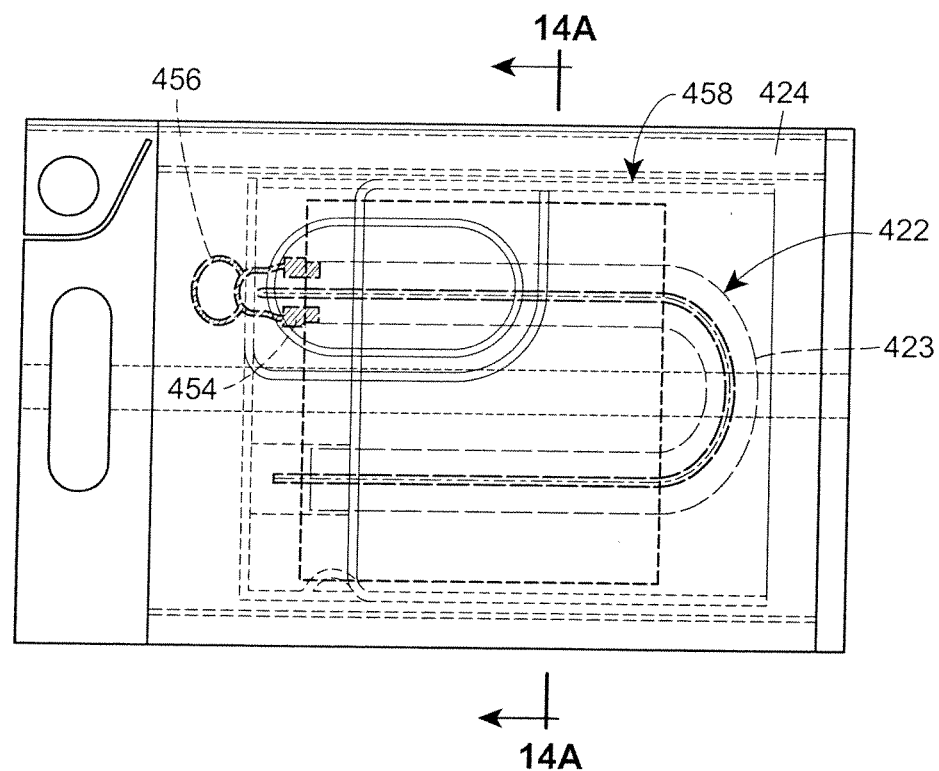
FIG. 14 is a diagrammatic plan view of still another alternative embodiment of a vapor hydrated catheter assembly.
Figure 14A:
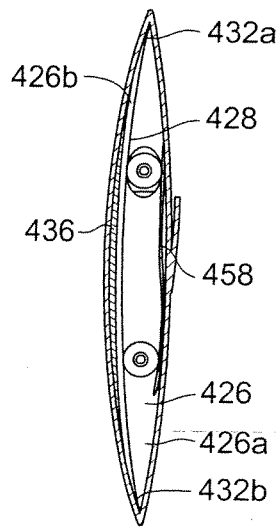
FIG. 14A is a diagrammatic cross-sectional view of the catheter assembly of FIG. 14 taken generally along the line 14A-14A thereof.

Referring to FIGS. 14 and 14A, it will be seen that the package 424 is also almost entirely structurally identical to the package 224 in FIGS. 12 and 12A and the package 324 in FIG. 13. The primary difference is that the embodiment of FIGS. 14 and 14A comprises a package 424 that contains a hydrophilic coated catheter 422 and urine collection bag assembly 458. The package 424 is still generally rectangular in shape, but the ratio of length to width will be considerably less than for the packages 224 and 324 which are designed for use with a catheter alone.

In other words, the package 424 has a size and shape to accommodate the typical size and shape of a urine collection bag assembly such as 458, that may be made from, for example, a polyethylene or PVC material. Unlike the long, narrow shape of typical catheter-only packages such as 224 and 324, the catheter 422 is folded into a generally U-shape within the package 424, thereby requiring a shorter but wider package for the assembly due to the shape of the collection bag assembly 458. While not important to the packaging, it will be seen that the catheter 422 has a "no-touch" sleeve 423, an insertion tip 454, and a protective cap 456.

With regard to all of the aforementioned embodiments and features, it will be understood that they are useful for all catheter product packages regardless of the exact size and shape and whether or not they are formed to hold catheters alone or to hold urine collection bag assemblies that incorporate a catheter therein. Thus, it will also be seen from FIGS. 14 and 14A that a wicking material 436 wetted with a liquid used as a quantity of water that can change into vapor capable of activating a hydrophilic coating on the catheter 422, and a gas permeable, liquid impermeable barrier 428 is heat sealed as at 432a and 432b to the inner surface of the sheet material in a manner sufficient to cover the wetted wicking material 436. In this manner, the sealed interior space 426 formed by the package 424 will have the urine collection bag assembly 458 and the hydrophilic coated catheter 422 in one cavity 426a and the liquid used to wet the wicking material 436 in another cavity 426b, whereby the hydrophilic coated catheter 422 is maintained out of direct contact with the liquid.

The present disclosure is also directed to a method of making a ready-to-use catheter assembly comprising the step of providing a catheter package having an interior space divided by a gas permeable, liquid impermeable barrier into a first cavity and a second cavity. The method includes the step of placing a catheter having a hydrophilic coating on at least a part of its length into the first cavity. The method further includes the steps of placing a liquid into the catheter package in liquid isolation relative to the first cavity and confining the liquid for selective liquid flow communication with the second cavity.

The method still further includes the steps of delaying distribution, or at least use, of the catheter assembly for a period of time sufficient for i) the liquid to be placed into selective liquid flow communication with the second cavity, ii) at least some of the liquid to change phase into vapor within the second cavity, iii) at least some of the vapor to pass from the second cavity, through the gas permeable, liquid impermeable barrier, and into the first cavity, and iv) the vapor in the first cavity to hydrate the hydrophilic coating to produce a low-friction surface on the catheter, whereby the catheter assembly is ready-to-use.

In addition, the method may include the steps of i) providing the liquid in a rupturable container communicating with the second cavity, and ii) providing a wicking material in the second cavity to absorb the liquid after the rupturable container is breached. Further, the method may include the step of breaching the rupturable container after the catheter package has been sealed in order to permit the liquid to be released so it can be drawn into and absorbed by the wicking material. Still additionally, the method may include the step of sterilizing the catheter and the liquid after the catheter package has been sealed but before the rupturable container has been breached.

In connection with the foregoing, the method may also comprise providing the rupturable container for the liquid as a self-contained rupturable container placed within the second cavity in spaced relation to the wicking material and in spaced relation to one end of the catheter. Alternatively, the method may comprise providing the rupturable container for the liquid as a rupturable compartment in the catheter package for selective liquid flow communication with the second cavity through a rupturable seal in spaced relation to the wicking material.

In addition to the foregoing, the method may also include the steps of forming the structure and components of the various embodiments and arranging them in relation to one another in the manner described in detail hereinabove.

The method may include the steps of breaching the rupturable container to release the liquid so it can be drawn into and absorbed by the wicking material. Next, the method may include the step of severing the catheter package between the catheter and the rupturable following absorption of the liquid by the wicking material. The method may include the step of thereafter forming an end seal for the catheter package.

The method may include the step of breaching a rupturable seal to release the liquid so it can be drawn into and absorbed by the wicking material. It will be appreciated in connection with some embodiments which have been described in detail hereinabove (e.g., FIGS. 7, 11, and 11A) that the liquid will pass through the intermediate compartment to the wicking material when the rupturable seal has been breached. It will also be appreciated that in these embodiments the method may include the step of severing the package through the intermediate compartment generally parallel to the intermediate seal following absorption of the liquid by the wicking material, preferably in spaced relation to the intermediate seal. Further, the method may include the step of thereafter forming an end seal for the catheter package.

In connection with the foregoing description of the method relative to the embodiments illustrated in FIGS. 7-11 and 11A, it will be appreciated that the steps of the method will be identical for both of the catheter assemblies with the exception that the wicking material will be separated from the catheter by a barrier in the form of a sleeve in the embodiment of FIGS. 7 and 11 whereas the wicking material will be separated from the catheter by a barrier in the form of a gas permeable, liquid impermeable mid-package film or membrane sheet captured by the side seals, an end seal, and an intermediate seal in the embodiment of FIG. 11A.

In addition to the foregoing, the method may also include making and using a ready-to-use catheter assembly which comprises the step of providing the catheter package with a tear tape affixed to the first cavity to cause the catheter package to tear along the tear tape. The method may include the step of sealing the catheter package to form a sealed interior space in which the first cavity and second cavity are sealed. The catheter package can be sealed with the first and second cavities in liquid isolation. The method may also include the step of placing the liquid in sealed confinement in the second cavity in liquid isolation relative to the first cavity. Further, it may include the step of using the tear tape to open the first sealed cavity along an intended opening line for access to the catheter in the first cavity without opening the second cavity.

In addition, the method of making and using a ready-to-use catheter assembly may also include providing the tear tape to extend within the first cavity in a desired direction relative to the catheter to cause the catheter package to open along the intended opening line. This facilitates removal of the catheter from the catheter package for use without opening the second cavity. Finally, the method of making and using a ready-to-use catheter assembly may include affixing the tear tape to an inner surface of the catheter package within the first cavity to extend generally from one end of the catheter package to the other end generally parallel to the catheter.

While the foregoing sets forth a detailed description of the preferred disclosure, it will be appreciated by those skilled in the art that the details herein given may be varied without departing from the true spirit and scope of the disclosure as set forth in the appended claims.

What is claimed is:

1. A catheter assembly comprising a catheter having a hydrophilic coating on at least a part of its length intended to produce a low-friction surface on the catheter when treated with a hydrating substance, a catheter package formed of a gas impermeable sheet material defining an interior space, a gas permeable, liquid impermeable mid-package film or membrane secured to the sheet material forming the catheter package, the mid-package film or membrane cooperating with the sheet material to physically divide the interior space in the catheter package into first and second cavities, the first cavity accommodating the catheter and the second cavity accommodating a wicking material and a rupturable container enclosing a quantity of liquid, the wicking material being disposed within the second cavity for liquid flow communication with the rupturable container to absorb the liquid when the rupturable container has been breached, the liquid absorbed by the wicking material being capable of changing phase into vapor capable of passing from the second cavity, through the gas permeable, liquid impermeable mid-package film or membrane, and into the first cavity, the vapor passing into the first cavity serving as the hydrating substance for treatment of the hydrophilic coating to produce the low-friction surface on the catheter.

2. The catheter assembly of claim 1 wherein the wicking material is disposed within the second cavity generally coextensive with the catheter and the package includes a seal extending inwardly from each side thereof between the catheter and the rupturable container to form a passageway for the liquid to pass through to the end of the wicking material.

3. The catheter assembly of claim 1 wherein the catheter package is formed to be of a generally elongated rectangular shape and the catheter and at least a major portion of the wicking material are disposed to extend at least substantially between the inwardly extending seal and an end of the catheter package located opposite the rupturable container.

4. The catheter assembly of claim 1 wherein the rupturable container is disposed in spaced relation to the wicking material for selective liquid flow communication with the wicking material.

5. A catheter assembly comprising a catheter having a hydrophilic coating on at least a part of its length intended to produce a low-friction surface on the catheter when treated with a hydrating substance, a catheter package formed of a gas impermeable sheet material defining an interior space, a gas permeable, liquid impermeable mid-package film or membrane secured to the sheet material forming the catheter package, the mid-package film or membrane cooperating with the sheet material to physically divide the interior space in the catheter package into first and second cavities, the first cavity accommodating the catheter and the second cavity accommodating a wicking material, the wicking material being disposed within the second cavity for liquid flow communication with a rupturable compartment for a quantity of liquid to absorb the liquid when the rupturable compartment has been breached, the liquid absorbed by the wicking material being capable of changing phase into vapor capable of passing from the second cavity, through the gas permeable, liquid impermeable mid-package film or membrane, and into the first cavity, the vapor passing into the first cavity serving as the hydrating substance for treatment of the hydrophilic coating to produce the low-friction surface on the catheter, and wherein the rupturable compartment is distinct from the first and second cavities.

6. The catheter assembly of claim 5 wherein the wicking material is disposed within the second cavity to extend generally coextensive with the catheter and a rupturable seal defines a boundary of the rupturable compartment, the catheter package including an intermediate seal disposed in spaced relation to the rupturable seal to define an intermediate compartment with the intermediate seal extending across the wicking material.

7. The catheter assembly of claim 5 wherein the catheter package is formed to have an intermediate compartment between the first and second cavities, on the one hand, and the rupturable compartment, on the other hand, the intermediate compartment extending between the wicking material and the rupturable compartment to define a space for receiving liquid from the rupturable compartment after a rupturable seal has been breached.

8. The catheter assembly of claim 6 wherein the wicking material has an end portion which extends from the second cavity through the intermediate seal into the intermediate compartment for wicking the liquid from the intermediate compartment into the second cavity.

* * * * *